US007049337B2

(12) United States Patent
Dutta (10) Patent No.: US 7,049,337 B2
(45) Date of Patent: May 23, 2006

(54) DERIVATIVES OF 2-AMINOTETRALINS AND PHARMACEUTICAL ANALOGS THEREOF EXHIBITING DIFFERENTIAL CNS RECEPTOR ACTIVITY AND BEHAVIOR

(75) Inventor: Aloke K. Dutta, Novi, MI (US)

(73) Assignee: Wayne State University, Detroit, MI (US)

( * ) Notice: Subject to any disclaimer, the term of this patent is extended or adjusted under 35 U.S.C. 154(b) by 214 days.

(21) Appl. No.: 10/276,641

(22) PCT Filed: May 17, 2001

(86) PCT No.: PCT/US01/15915

§ 371 (c)(1),
(2), (4) Date: Apr. 21, 2003

(87) PCT Pub. No.: WO01/89453

PCT Pub. Date: Nov. 29, 2001

(65) Prior Publication Data

US 2003/0225154 A1 Dec. 4, 2003

Related U.S. Application Data

(60) Provisional application No. 60/205,779, filed on May 19, 2000.

(51) Int. Cl.
*A61K 31/136* (2006.01)
*A61K 31/381* (2006.01)
*C07C 211/42* (2006.01)
*C07D 333/20* (2006.01)

(52) U.S. Cl. .................. 514/438; 514/657; 549/75; 558/394; 564/428

(58) Field of Classification Search .................. 549/75; 558/394; 564/428; 514/438, 657
See application file for complete search history.

(56) References Cited

U.S. PATENT DOCUMENTS 5,196,454 A * 3/1993 Grauert et al. .............. 514/654
5,545,755 A 8/1996 Lin et al.
5,690,906 A * 11/1997 Kung ........................ 424/1.85

FOREIGN PATENT DOCUMENTS

WO WO-99/62505 * 12/1999

OTHER PUBLICATIONS

Chumpradit et al., Journal of Medicinal Chemistry, 36(26), 4308-4312, 1993.*
Chumpradit et al., Journal of Medicinal Chemistry, 37(24), 4245-4250, 1994.*
O. Civelli et al., "Molecular Diversity of the Dopamine Receptors," Annu. Rev. Pharmacol. Toxicol., 32, 281-307, 1993.

N.E. Austin et al., "Novel 2,3,4,5-Tetrahydro-1H-3-benzazepines with High Affinity and Selectivity for the Dopamine $D_3$ Receptor," Bio. Med. Chem. Ltrs, (2000) 2553-2555.
P. Seeman et al., "Dopamine Receptor Pharmacology," TIPS, 15, 264-270, 1994.
J.W. Kebabian et al., "Multiple Receptors for Dopamine," Nature, 277, 93-96, 1979.
S.G. Caine et al., "Modulation of Cocaine Self-Administration in the Rat through D-3 Dopamine Receptors," Science, 260, 1914-1916, 1993.
S.B. Caine et al., "Pretreatment with the Dopamine Agonist 7-OH-DPAT Shifts the Cocaine Self-Administration Dose Effect Function to the Left Under Different Schedules in the Rat," Behav. Pharmacol., 6, 33-347, 1995.
H.H.M. Van Tol et al., "Cloning of the Gene for a Human Dopamine D4 Receptor with High Affinity for the Antipsychotic Clozapine," Nature, 350, 610-614, 1991.
D. Levesque et al., "Identification, Characterization, and Localization of the Dopamine D3 Receptor in Rat Brain Using 7 [$^3$H] hydroxy-N,N-di-n-propyl-2-aminotetralin," Proc. Natl. Acad. Sci. U.S.A., 89, 8155-8159, 1992.
T.A. Pugsley et al., "Neurochemical and Functional Characterization of the Preferentially Selective Dopamine D3 Agonist PD 128907," Pharmacol. Exp. Ther., 275, 1355-1366, 1995.
R.G. MacKenzie et al., "Characterization of the Human Dopamine D3 Receptor Expressed in Transfected Cell Lines," Eur. J. Pharmacol., 266, 79-85, 1994.
P. Sokoloff et al., "Molecular Cloning and Characterization of a Novel Dopamine Receptor (D3) as a Target for Neuroleptics," Nature, 347, 146, 1990.
J.G. Canon et al, "Centrally Acting Emetics. 6. Derivatives of β-Naphthylamine and 2-Indanamine," J. Med. Chem., 15, 348-350, 1972.
J.G. Canon et al., "Cerebral Dopamine Agonist Properties of Some 2-Aminotetralin Derivatives after Peripheral and Intracerebral Administration," J. Med. Chem., 20, 1111-1116, 1977.
J. McDermed et al., "Synthesis and Pharmacology of Some 2-Aminotetralins Dopamine Receptor Agonists," J. Med. Chem., 18, 362-367, 1975.
J.D. McDermed et al., "Synthesis and Dopaminergic Activity of (+), (+)-, and (−) -2-Dipropylamino-5-hydroxy-1,2,3,4-tetrahydronaphthalene," J. Med. Chem., 19, 547-549, 1976.

(Continued)

*Primary Examiner*—Fiona T. Powers
(74) *Attorney, Agent, or Firm*—Brooks Kushman P.C.

(57) ABSTRACT

Aminotetralin derivatives and pharmacological analogs thereof which contain an N-propynyl group exhibit differential dopaminergic receptor activity. The subject compounds are useful in affecting dopamine receptor activity, particularly in exhibiting differing activity among the various dopamine receptor subtypes. The compounds are useful in treating CNS disorders in mammals in general, and humans in particular.

31 Claims, 2 Drawing Sheets

OTHER PUBLICATIONS

U. Hacksell et al., "N-alkylated 2-Aminotetralins: Central Dopamine-Receptor Stimulating Activity," J. Med. Chem., 22, 1469-1475, 1979.

L. Alexander Van Vliet et al., "Affinity for Dopamine D2, D3 and D4 Receptors of 2-Aminotetralins. Relevance of D2 Agonist Binding for Determination of Receptor Subtype Selectivity," J. Med. Chem., 39, 4233-4237, 1996.

M.S. Starr et al., "Motor Actions of 7-OH-DPAT in Normal and Reserpine-Treated Mice Suggest Involvement of Both Dopamine D2 and D3 Receptors," Eur. J. Pharmacol., 277, 151-158, 1995.

V.J. Watts et al., Eur. J. Pharmacol., 1993, 239, 271.

M.E.A. Reith et al., Biol. Chem., 1986, 261, 7300.

Khroyan et al., "Dose-Dependent Effects of the D3—preferring agonist 8-OH-DPAT on Motor Behaviors and Place Conditioning," Psychopharmacol. 122:351-57 (1995).

* cited by examiner

DERIVATIVES OF 2-AMINOTETRALINS AND PHARMACEUTICAL ANALOGS THEREOF EXHIBITING DIFFERENTIAL CNS RECEPTOR ACTIVITY AND BEHAVIOR

This application is the U.S. national phase of PCT application number PCT/US01/15915, filed May 17, 2001, which further claims the benefit of U.S. provisional application Ser. No. 60/205,779, filed May 19, 2000.

TECHNICAL FIELD

The present invention pertains to novel organic compounds which exhibit differential CNS activity, in particular differential dopaminergic behavior, and to the treatment of central nervous system (CNS) disorders by administering such compounds or a pharmaceutically acceptable salt or derivative thereof to a mammal in need of such treatment.

BACKGROUND ART

The importance of dopamine in CNS activity is well recognized, and dopamine receptors have been important targets for drug development. O. Civelli et al., "Molecular Diversity of the Dopamine Receptors", ANNU. REV. PHARMACOL. TOXICOL. 32, 281–307, 1993; P. Seeman et al., "Dopamine Receptor Pharmacology", TIPS, 15, 264–270, 1994. Detailed investigation has recently revealed the existence of several subtypes of dopamine ("DA") receptors. See Civelli, op. cit., Seeman, op. cit., and J. W. Kebabian et al., "Multiple Receptors for Dopamine", NATURE, 277, 93–96, 1979. From cloning of DA receptor forms and isoforms, two main D1-like (D1 and D5) and D2-like (D2, D3, and D4) categories of DA receptors can be identified. Civelli, op. cit., Seeman, op. cit.

Of the receptor subtypes, the D3 receptor is distributed in the limbic area of the human brain, but absent from the caudate and putamen. This distribution makes the D3 receptor a potential target for drugs with an unusual spectrum of activities, in particular, CNS activities focused on specific disorders. For example, D3 antagonists may exhibit activity as atypical antipsychotic agents. D3 agonists have potential application in the therapeutic treatment for Parkinson's disease. B. Giros et al., ACAD. SCI [III] 1990, 311, 501. Recent studies suggest that D3 specific compounds may be useful in treating cocaine addition. S. G. Caine et al., "Modulation of Cocaine Self-administration in the Rat through D-3 Dopamine Receptors", SCIENCE, 260, 1914–1816, 1993; S. B. Caine et al., "Pretreatment With The Dopamine Agonist 7-OH-DPAT Shifts the Cocaine Self-administration Dose Effect Function to the Left Under Different Schedules in the Rat", BEHAV. PHARMACOL. 6, 33–347, 1995; D. B. Calne et al., "Therapeutics and Neurology", BLACKWELL SCIENTIFIC PUBLICATIONS, Oxford, 1980.

Several CNS drugs and drug candidates have been developed which exhibit selectivity for the D1 or D2 families of DA receptors. Some of these compounds have been shown to also exhibit limited selectivity for DA receptor subtypes. For example, clozapine, an atypical psychotic agent, exhibits preferential antagonist activity for the D4 receptor, and is now used in treating schizophrenia. H. H. M. Van Tol et al., "Cloning of the Gene for a Human Dopamine D4 Receptor with High Affinity for the Antipsychotic Clozapine". NATURE, 350, 610–614, 1991. Several D2 agonists, for example 7(+)-OH-DPAT, (+)PD 128907 and quinpirole have recently been shown to have preferential affinity for the D3 receptor. D. Levesque et al., "Identification, Characterization, and Localization of the Dopamine D3 Receptor in Rat Brain Using 7-[$^3$H]hydroxy-N,N-di-n-propyl-2-aminotetralin. PROC. NATL. ACAD. SCI. U.S.A. 89, 8155–8159, 1992; T. A. Pugsley et al., "Neurochemical and Functional Characterization of the Preferentially Selective Dopamine D3 Agonist PD 128907, PHARMACOL. EXP. THER. 275, 1355–1366, 1995; R. G. MacKenzie et al., "Characterization of the Human Dopamine D3 Receptor Expressed in Transfected Cell Lines". EUR. J. PHARMACOL., 266, 79–85, 1994. The ability to exhibit differential activity with respect to different DA receptor subtypes can significantly alter treatment possibilities. In addition to the expected consequence of achieving unique CNS response due to the stimulation of but one receptor subtype rather than several, it is also conceivable that differential dopaminergic drugs having differential effects might be used in "push-pull" fashion, i.e., one drug which is an antagonist for the D3 receptor in combination with an agonist or antagonist for another receptor, but which does not affect the D3 receptor. Such strategies cannot be used when drug candidates do not display differential activity.

Much progress has been made in dopaminergic response at the D3 receptor since its cloning in 1990. P. Sokoloff et al., "Molecular Cloning and Characterization of a Novel Dopamine Receptor (D3) as a Target for Neuroleptics", NATURE, 347, 146, 1990. Several specific compounds have been identified which are relatively selective for the D3 receptor. The majority of these compounds belong to the class of 2-aminotetralins. J. G. Canon et al., "Centrally acting Emetics. 6. Derivatives of β-Naphthylamine and 2-Indanamine", J. MED. CHEM. 15, 348–350, 1972; J. G. Canon et al., "Cerebral Dopamine Agonist Properties of Some 2-Aminotetralin Derivatives after Peripheral and Intracerebral Administration", J. MED. CHEM. 20, 1111–1116, 1977; J. McDermed et al., "Synthesis and Pharmacology of Some 2-Aminotetralins. Dopaminae Receptor Agonists", J. MED. CHEM., 18, 362–367, 1975; J. D. McDermed et al., "Synthesis and Dopaminergic Activity of (±)-, (+)-, and (−)-2-Dipropylamino-5-hydroxy-1,2,3,4-tetrahydronaphthalene", J. MED. CHEM. 19, 547–549, 1976; U. Hacksell et al., "N-alkylated 2-Aminotetralins: Central Dopamine-Receptor Stimulating Activity", J. MED. CHEM. 22, 1469–1475, 1979. Further studies have investigated large numbers of 5-hydroxy-2-amninotetralin derivatives, and systematic screening has identified several drug candidates with at least some D3 selectivity. L. Alexander Van Vliet et al., "Affinity for Dopamine D2, D3 and D4 Receptors of 2-Aminotetralins. Relevance of D2 Agonist Binding for Determination of Receptor Subtype Selectivity", J. MED. CHEM. 39, 4233–4237, 996.

SAR studies have shown that both 7-hydroxy and 5-hydroxy derivatives of 2-aminotetralin are active at the D2L and D3 receptors, with 7-hydroxy-2-aminotetralins exhibiting preferential affinity for the D3 receptor as compared to their 5-hydroxy analogous. Further, while both 5-hydroxy- and 7-hydroxy-2-aminotetralins exhibited dopaminergic behavior, 8-hydroxy analogs produced serotoninergic activity. Binding assays also make clear that different optical isomers display different activities. J. D. M. McDermed et al., op. cit.

In the class of hydroxy-substituted-2-aminotetralins, it has been believed that at least one n-propyl group is necessary as an amino group substituent to confer significant receptor activity. The nature of the second amino nitrogen substituent is apparently less important based on these studies, although some studies have shown that bulky alkylaromatic substituents increase activity. The importance of at least one N-(n-propyl) group and preferably two n-propyl groups can be shown by R(+)-7-OH-DPAT, Pramipexole, (+)-PD 128907, and (+)-S-14297, which have structures I through IV, respectively:

All these compounds possess two N-(n-propyl) groups or, in the case of III, a closely related structure. All exhibit some preference for the D3 receptor. However, their differential binding capacity is limited, and appears to vary with the nature of the receptor binding state. For example, I was found to be about 100 times more selective for the D3 receptor as compared to the D2 receptor when displacing [$^3$H]spiperone under experimental conditions which favored a low affinity D2 state. However, I was only 60 times more selective when the high affinity states of D2 and D3 receptors were compared. Based both on these studies and on behavioral studies, it is believed that in vivo, I binds to the D3 receptor at low concentration, but at higher concentration becomes non-selective. M. S. Starr et al., "Motor Actions of 7-OH-DPAT in Normal and Reserpine-Treated Mice Suggest Involvement of Both Dopamine D2 and D3 Receptors". EUR. J. PHARMACOL. 277, 151–158, 1995. Thus, for drug candidates which exhibit behavior similar to I, unless the compound exhibits high activity at very low concentration, the desired selectivity between receptors will be lost when the concentration is increased to pharmacogically useful levels.

Compound III and Nafadotride, the latter not related chemically to aminotetralins, have recently been shown to be among the most potent D3 antagonists. Although these compounds show some preference for binding to the D3 receptor, they still exhibit a high affinity to the D2 receptor as well.

In Lin et al. U.S. Pat. No. 5,545,755, an enormously large number of 2-aminotetralins are disclosed which may have either serotoninergenic or dopaminergenic activity. However, only selectivity between the 5-HT$_{1A}$ (5-hydroxytryptamine) receptor and dopamine D2 receptor is disclosed; no selectivity between seratonin and dopamine receptors or between dopamine subtype receptors is reported.

It is well known in the pharmaceutical industry that drug pharmacology can vary considerably between different patients. A drug candidate which is highly effective in one patient may be ineffective in others. In some cases, drug allergies or unintended and unwanted side effects may mitigate against prescribing a drug to certain individuals. Thus, it would be desirable to provide additional dopaminergenic and serotoninergic drug candidates of high activity which are different chemically and/or pharmacologically from those developed previously. It would also be desirable to provide drug candidates which exhibit differential binding activities, especially between dopamine receptor subtypes. It would be yet further desirable to provide drug candidates in which the selectivity between receptors is higher than presently available.

DISCLOSURE OF INVENTION

It has now been surprisingly discovered that N-(2'-propynyl)-substituted 2-aminotetralins and bioisosterically related compounds are not only potent CNS drug candidates, but exhibit high selectivity between receptor subtypes as well.

BEST MODE FOR CARRYING OUT THE INVENTION

The differential CNS active compounds of the present invention correspond to the formula (A)

and to bioisosteric analogs of this structure containing the N-(2'-propynyl) moiety. Broadly, in this structure, $R^1$ and $R^2$ together form a 5 or 6 member aromatic ring structure which may contain up to 3 heteroatoms selected from N, O, and S, and which may be optionally substituted at substitutable ring position, including substituents which together comprise a 4 to 8 membered aromatic or saturated or unsaturated cycloaliphatic ring structure, this 4 to 8 membered aromatic or cycloaliphatic ring structure also optionally containing from 1 to 3 heteroatoms selected from N, O, and S. The cycloaliphatic ring structure may contain one or two sites of ethylenic unsaturation, and may be polycyclic, i.e., bridged, as well. The 4 to 8 membered aromatic or cycloaliphatic ring may optionally be substituted. X is preferably carbon, but may also be N, O, or S, preferably O. The number n of methylene units is 0 or 1, preferably 0. R may be H, alkyl, cycloalkyl, aryl, or other hydrocarbon-containing structures, optionally substituted.

In general the compounds of the present invention correspond to 2-aminotetralins or biosteric analogs thereof containing a fused ring structure, one ring comprising an optionally ring substituted moiety or a pharmaceutically acceptable salt or derivative of such a compound, wherein X is $CH_2$, O, NH, or S, n is 0 or 1, and

R is ethyl, butyl, or a $C_{5-20}$ hydrocarbon, each optionally substituted by one or more halo, nitro, amino, aminoalkyl, or cyanogroups, or R is a halo-, nitro-, amino-, cyano- or aminoalkyl-substituted propyl group, R optionally containing one or more heteroatoms selected from the group consisting of O, N, and S, and which may contain a keto, thio, ester, carbonate, urea, amide, or urethane group.

Preferred compounds correspond to compounds of the formula (I)

wherein $R^1$ and $R^2$ together complete a 5 membered aromatic ring optionally containing up to 2 heteroatoms individually selected from the group consisting of O, N, and S, and optionally substituted by $R^3$, $R^4$, and $R^5$ at substitutable ring positions:

or a 6 membered aromatic ring optionally containing up to three heteroatoms individually selected- from the- group of O, N, and S, and optionally substituted by $R^3$, $R^4$, $R^5$, and $R^6$ at substitutable ring positions:

$R^3$, $R^4$, $R^5$, and $R^6$ are individually selected from H, $C_{1-18}$ alkyl, $C_{2-8}$ alkenyl, —OH, —$OR^{11}$, $NH_2$, —$NHR^{11}$, —$NHR_2^{11}$, —CN, —$SO_2H$, =O, =NH, =$NR^{11}$, —NH—CO—$NH_2$, —NH—CO—$NHR^{11}$, and NH—CO—$NR_2^{11}$, or any adjacent $R^3$ through $R^6$ may form a saturated, unsaturated, or aromatic 5 to 7 membered ring, optionally containing one to three heterocycles selected from the group consisting of N, O, and S, $R^7$, $R^8$, $R^9$, and $R^{10}$ are individually selected from H, $NR_2^{11}$, $C_{1-18}$ alkyl, $C_{2-18}$ alkenyl, $C_{3-8}$ cycloalkyl, $C_{3-8}$ cycloalkenyl, $C_{3-8}$ aryl, $C_{6-14}$ heteroalkyl $C_{1-4}$ lower alkoxy, all of the alkyl, alkenyl, cycloalkyl, cycloalkenyl, aryl, and heteroaryl groups optionally substituted by $R^{12}$ or the pair $R^7$ and $R^8$ or the pair $R^9$ and $R^{10}$ may individually as pairs be =O, —NH, or =NR", where $R^{12}$ is —OH, —$OR^{11}$, —$NHR^{11}$, —O—C—$NHR^{11}$, —$SO_2H$, $SO_2R^{11}$, F, Cl, Br, $F_3C$—, —CN, or —$NO_2$, where $R^{11}$ is $C_{1-18}$ alkyl, $C_{2-18}$ alkenyl, $C_{3-8}$ cycloalkyl, $C_{3-8}$ cycloalkenyl, $C_{6-10}$ aryl, $C_{6-10}$ heteroaryl, each of R" optionally substituted by $C_{1-4}$ lower alkyl, —OH, and —$NH_2$, and wherein each alkyl, alkenyl, or cycloalkyl or alkenyl substtuent may be interrupted by one or more non-adjacent heteroatoms selected from the group consisting of N, O, and S, or a pharmaceutically acceptable salt or derivative thereof.

In certain preferred embodiments corresponding to the above structures, X is $CH_2$ and Y is CH, $R^{14}$ is H, each of $R^7$ through $R^{10}$ is H, and R is propyl, 3-cyanopropyl, 4'-fluorophenyl, or thienylethyl.

More preferably, the differential CNS active compounds of the present invention correspond to structures (B), (C) or (D) below:

In these and other structures, each of $R^3$–$R^{10}$ may be selected individually. $R^7$–$R^{10}$ are preferably H, —$NR^{11}_2$ or $C_{1-4}$ lower alkyl, or $R^7$ and $R^8$ together and/or $R^9$ and $R^{10}$ together may be keto (=O), thio (=S), imino (=NH) or substituted imino (=$NR^{11}$). Most preferably, $R^7$–$R^{10}$ are H. Less preferably, $R^7$–$R^{10}$ may be $C_{1-18}$ alkyl, $C_{2-18}$ alkenyl, $C_{3-8}$ cycloalkyl, $C_{3-8}$ cycloalkenyl, $C_{6-14}$ aryl, $C_{6-14}$ heteroaryl, and like. The alkyl, cycloalkyl, aryl, etc., groups may be unsubstituted, or may be substituted by $R^{12}$, defined to include or by $R^{13}$, defined to include fluoro, chloro, bromo, trifluoromethyl, or nitro. In addition, the cycloaliphatic and aliphatic substituents $R^7$–$R^{10}$ may be interrupted by heteroatoms including O, S, and NH, i.e., they may contain one or more ether, thioether, or secondary amino linkages. More preferably, at least two, and yet more preferably at least three of $R^7$–$R^{10}$ are H. In the above formulae, $R^{11}$ is defined as $C_{1-18}$ alkyl, $C_{2-18}$ alkenyl, $C_{3-8}$ cycloalkyl, $C_{3-8}$ cycloalkenyl, $C_{6-10}$ aryl and $C_{6-10}$ heteroaryl, each of these structures optionally substituted by $C_{1-4}$ lower alkyl, preferably methyl; hydroxyl; amino; or cyano. $R^{11}$ is preferably hydrogen or $C_{1-4}$ lower alkyl.

In structure (B), it is preferable that at least one of $R^3$ to $R^6$ is hydroxyl. In a further preferred embodiment, all of $R^3$–$R^6$ are hydrogen. In general, however, each of $R^3$ to $R^6$ may be defined as $R^7$ to $R^{10}$ have been defined previously. In addition, in structures (B) and (C), one or more of $R^3$–$R^6$ may be a keto or imino group, provided that aromaticity of the ring structure is not lost thereby. Any two of $R^3$ to $R^6$, where possible within the geometrical constraints of the molecule, may together form a saturated or unsaturated cycloaliphatic or aryl ring system, with or without ring heteroatoms. The cycloaliphatic and aryl ring systems may be substituted by $R^{11}$, $R^{12}$ or $R^{13}$ substituents as defined above. Examples of the latter compounds are Preferably, the differential CNS active compounds of the present invention correspond to where Y is OH and Z is F or Cl. Yet more preferably Y is 5-OH or 7-OH and Z is 6-F or 6-Cl. X is preferably $CH_2$ or O.

In all of the foregoing, R may be as previously defined, for example, H, $C_{1-18}$ hydroxyalkyl, $C_{6-10}$ aryl, $C_{6-10}$ heteroaryl, $C_{7-18}$ alkaryl, $C_{7-18}$ aralkyl. Each of the groups above with the exception of hydrogen may be substituted with halo, nitro, amino, aminoalkyl, or cyano groups, and may have attached thereto an $R^{12}$ substituent as defined previously. Most preferably, R is ethyl, propyl, butyl, benzyl, phenylethyl, 2-(4'-fluorophenyl)ethyl, thienyl, thienylethyl, or 3-cyanopropyl. Most preferably, R is 3-cyanopropyl or 2-thienylethyl. In particular, the differential CNS active compounds:

have been shown to exhibit differential binding capacity for the D3 receptor which is considerably higher than previously disclosed compounds.

Illustrative ring systems which the subject differential CNS compounds are based include the following, with "$N_R$" being the point of attachment of the propynyl-substituted amino group or the propynyl-substituted aminomethylene group -continued Of the foregoing, ring systems E, F, L, P and O are particularly preferred.

The compounds of the subject invention may be administered to mammals for treatment of CNS disorders. A "CNS disorder" is defined broadly herein as CNS function activity, or property which is desired to be changed by pharmacological means. The CNS function may be expressed in numerous ways. Certain CNS disorders belong to recognized classes in the field of medicine, for example schizophrenia, attention deficit disorder (ADD), attention deficit hyperactivity disorder (ADHD), Parkinson's disease, dystonia, basal ganglia disorder, cocaine addiction, Huntington's disease, and the like. Classes of drugs involved, based on pharmacology, not on chemical structure, include neuroleptics, atypical antipsychotics, analgesics, stimulants, etc.

In addition to the treatment per se of CNS disorders, the differential CNS compounds have utility for altering CNS properties, for example as radio-imaging agents in applications of single photon emission computed tomography (SPECT) or photon emission tomography (PET). The use of compounds for these applications is also considered "treatment" as that term is used herein, unless indicated to the contrary.

The therapeutically active dosages will depend upon numerous factors, including but not limited to the specific disorder treated or change in response desired; the specific compound; whether the compound is optically pure or is racemic; the solubility in vivo; the rate of metabolization into non-active (or differently active forms); the rate of excretion; the ability to permeate various membranes, etc. Dosage may be determined by the same techniques used for other CNS drug candidates.

Preferred therapeutically useful doses for the subject differential CNS compounds range from 0.001 to 50 mg/Kg body weight, more preferably 0.01 to 10 mg/Kg body weight when administered orally, and 0.5 to 100 mg total dosage when administered parenterally. Preferred serum levels range upwards from 1 nM to about 10 µM. Higher fluid concentrations may be indicated in some cases, while lower levels may be useful for candidates of exceptional potency. The proper dosage level is readily determined by one skilled in the art.

Figure 1A:
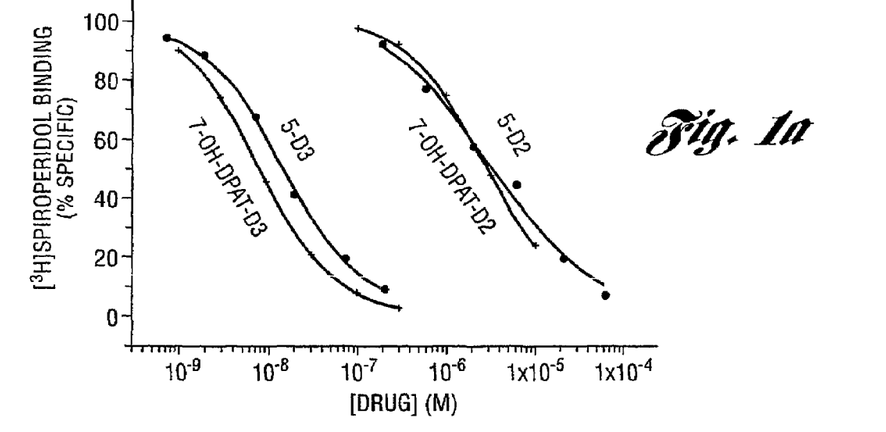
FIGS. 1a–1c illustrate inhibition curves of a control (7-OH-DPAT) and several compounds of the subject invention with respect to D2 and D3 receptors.
Figure 1B:
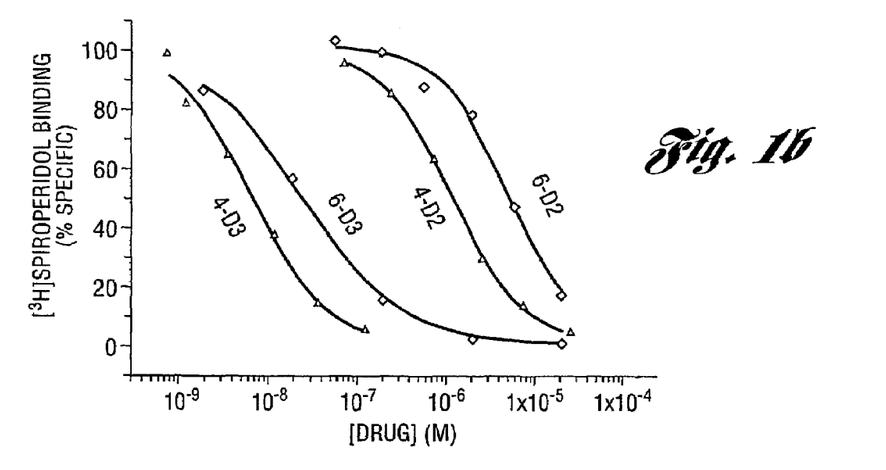
Figure 1C:
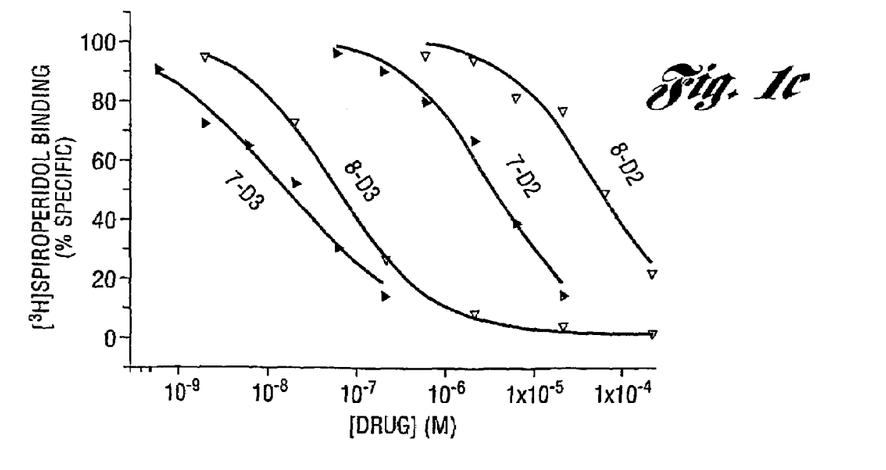
Figure 2A:
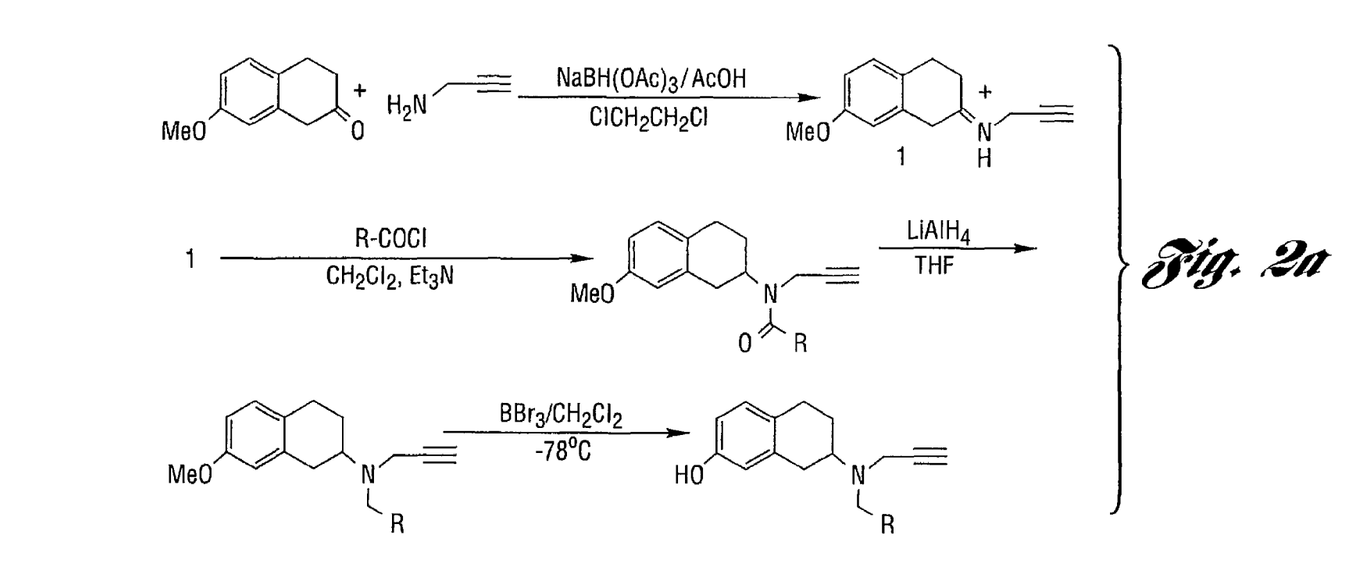
FIGS. 2a and 2b illustrate synthetic pathways to certain of the compounds of the present invention.
Figure 2B:
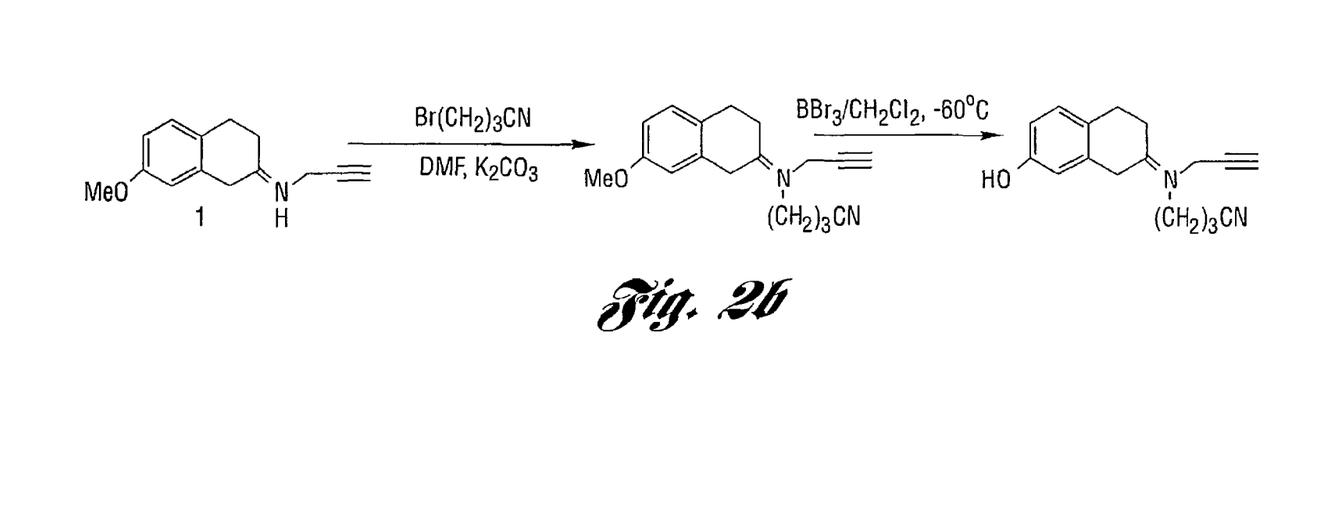

The subject differential CNS compounds are readily synthesized by conventional organic synthetic techniques. Synthetic pathways for five specific compounds are given as FIGS. 2 through 5, which are self explanatory. Further information relative to synthesis may be gleaned from the Examples which are presented later herein.

The target compounds synthesized were assayed for differential CNS activity by binding studies employing cloned human receptors expressed in HEK cells. A reference compound, (+)-7-OH-DPAT was used as a control. The compounds were evaluated for their binding at the D2 and D3 receptors.

Analytical silica gel-coated TLC plates (Si 250F) were purchased from Baker, Inc. and were visualized with UV light or by treatment with phosphomolybdic acid (PMA). Flash chromatography was carried out on Baker Silica Gel 40 mM. $^1$H NMR spectra were routinely obtained at 100 MHZ on a Bruker WP-100-SY instrument. The NMR solvent used was $CDCl_3$ as indicated. TMS was used as an internal standard. Elemental analyses were performed by Atlantic Microlab, Inc. and were within ±0.4% of the theoretical value.

Having generally described this invention, a further understanding can be obtained by reference to certain specific examples which are provided herein for purposes of illustration only and are not intended to be limiting unless otherwise specified.

EXAMPLE 1

Synthesis of (R,S)-trans-7-methoxy-2-[N-(propynyl) amino]tetralin

The reductive amination of 7-methoxytetralone with propargyl amine in the presence of sodium triacetoxyborohydride and acetic acid furnished (R,S)-trans-7-methoxy-2-[N-(propynyl)amino]tetralin, 1, (Scheme 1) in good yield. Thus a mixture of 7-methoxy-2-tetralone (1.5 g, 8.5 mmol), propargyl amine (0.8 g, 10.8 mmol), sodium triacetoxyborohydride (3 g, 14 mmol) and glacial acetic acid in 30 mL of 1,2-dichloroethane were stirred at room temperature overnight. The solution was filtered and the crude product was chromatographed over a silica gel column. The pure product was recrystallized from (1:4) EtOAc/hexane mixture, 1.57 g (84% yield).

$^1$H NMR ($CDCl_3$): 3.1–2.1 (3H, m), 2.2 (1H, t), 2.45–3.32 (5H, m), 3.55 (2H, d), 3.76 (3H, s), 6.65–7.05 (3H, m).

EXAMPLE 2

Synthesis of (R,S)-trans-7-methoxy-2-[N-(propynyl)-N-butyro)amino]tetralin, 2a

The compound of Example 1 (0.2 g, 0.92 mmol) was reacted with butyryl chloride (0.14 g, 0.69 mmol) in 50 mL methylene chloride in the presence of $Et_3N$ chilled by an ice water bath. The reaction was continued for 3 hours and the solvent removed in vacua. The crude product was dissolved in ethyl acetate and extracted with saturated aqueous sodium bicarbonate. The organic layer was dried over anhydrous sodium sulfate, and chromatographed over a silica gel column. The pure compound was eluted with 1:4 EtOAc: hexane, yielding (R,S)-trans-7-methoxy-2-[N-(propynyl)-N-butyro)amino]tetralin in very good yield, 0.22 g (85% yield).

$^1$H NMR ($CDCl_3$): 0.9–1.1 (3H, t, J=), 1.6–2.55 (8H, m), 2.85–3.05 (3H, m), 3.76 (3H, s), 4.05–4.15 (3H, m), 6.6–7.05 (3H, m).

EXAMPLE 3

Synthesis of (R,S)-trans-7-methoxy-2-[N-propynyl-N-(butyl-amino]tetralin

Lithium aluminum hydride (0.085 g, 2.2 mmol) was suspended in 30 mL dry THF, and the solution was cooled in an ice bath. Amide 2a (0.21 g, 073 mmol), dissolved in 10 mL of tetrahydrofuran (THF), was added dropwise into the cold solution. The solution was refluxed for 2 h, and after cooling (ice bath) unreacted lithium aluminum hydride was quenched by careful addition of an excess amount of 10% NaOH solution. The solution was filtered and the residue was repeatedly washed with an excess amount of ethyl acetate (EtOAc). The combined extract was dried over $Na_2SO_4$ and the crude product was collected. The pure product, 3a, was eluted with 20% EtOAc in hexane mixture, 0.14 g (74% yield), as a colorless liquid.

$^1$H NMR ($CDCl_3$): 0.85–0.99 (3H, t, J=), 1.25–1.78 (5H, m), 2.14–2.19 (3H, m), 2.59–2.93 (6H, m), 3.50–3.53 (2H, d, J=), 3.76 (3H, s), 6.63–7.03 (3H, m).

EXAMPLE 4

Synthesis of (R,S)-trans-7-Hydroxy-2-[N-propynyl-N-(butyl-amino]tetralin

Demethylation of the product of Example 3 with $BBr_3$ at −78° C. under basic work up (pH=8) conditions provided (R,S)-trans-7-hydroxy-2-[N-propynyl-N-(butyl-amino]tetralin in good yield. Thus, the compound produced in Example 3 (0.14 g, 0.51 mmol) was dissolved in methylene chloride and cooled to −78° C., into which was added 1 M boron tribromide (0.77 mL, 0.77 mmol). The solution was gradually warmed to room temperature and was stirred at room temperature for 2 hrs. The reaction mixture was carefully quenched under basic conditions and the crude product extracted into EtOAc. The crude product was chromatographed over a silica gel column and the pure product was eluted from the column with 50% EtOAc:hexane mixture. Obtained was 0.075 g (50% yield).

$^1$H NMR ($CDCl_3$): 0.86–0.99 (3H, t, J=), 1.26–1.8 (5H, m), 2.16–2.21 (3H, m), 2.62–3.00 (6H, m), 3.53–3.55 (2H, d, J=), 6.53–6.96 (3H, m). The free base was converted into its hydrobromide salt. Anal. ($C_{17}H_{23}NO$. HBr)C, H, N.

EXAMPLE 5

Synthesis of (R,S)-trans-7-Hydroxy-2-[N-propynyl-N-ethyl-amino]tetralin (R,S)-trans-7-methoxy-2-[N-(propynyl)amino]tetraline from Example 1 (0.26 g, 1.2 mmol) was reacted with acetyl chloride (0.17 g, 2.1 mmol) to furnish (R,S)-trans-7-methoxy-2[(N-acetoxy-N-propynyl)aminotetralin 0.18 g (60% yield) as a colorless oil (Procedure A). $^1$H NMR (CDCl$_3$): 1.75–2.25 (6H, m), 2.75–2.95 (4H, m), 3.76 (3H, s), 4.00–4.18 (3H, m), 6.64–7.10 (3H, m).

The N-acetoxy-N-propynyl aminotetralin produced (0.17 g, 0.66 mmol) was reacted with lithium aluminum hydride (0.075 g, 1.9 mmol) to furnish (R,S)-trans-7-methoxy-2-[(N-ethyl-N-propynyl)amino] 0.18 g (98%) as a colorless oil (Procedure B). $^1$H NMR (CDCl$_3$): 1.05–2.00 (3H, t, J=), 1.5–2.25 (3H, m), 2.65–3.10 (7H, m), 3.56 (2H, d), 3.76 (3H, s), 6.65–7.05 (3H, m).

The demethylation of the N-ethyl-N-propynyl aminotetralin (0.2 g, 0.82 mmol) was conducted in presence of boron tribromide (1.2 mL) to produce final product (R,S)-trans-7-hydroxy-2[(N-ethyl-N-propynyl)amino] 0.12 g (66%) as a colorless oil (Procedure C). $^1$H NMR (CDCl$_3$): 1.05–1.22 (3H, t, J=), 1.46–2.25 (3H, m), 2.6–3.04 (7H, m), 3.56 (2H, d), 6.54–7.00 (3H, m). The free base was converted into its hydrobromide salt. Anal. ($C_{15}H_{19}NO$. HBr. 0.2 $H_2O$)C, H, N.

EXAMPLE 6

Synthesis of (R,S)-trans-7-Hydroxy-2-[N-propynyl-N-ethyl(4'-fluorophenyl)amino]tetralin 4-Fluorophenyl acetic acid was converted into the acid chloride by reaction with acetyl chloride, and subsequently (0.7 g, 2 mmol) reacted with (R,S)-trans-7-methoxy-2-[N-propynyl)amino]tetralin (0.45 g, 2 mmol) to produce the corresponding amide, 0.41 g (59% yield) as a colorless oil. $^1$H NMR (CDCl$_3$): 1.61–2.05 (9H, m), 3.77 (3H, s), 3.85–4.13 (3H, m), 6.58–7.26 (7H, m).

The amide (0.35 g, 0.9 mmol) on reduction with LiAlH$_4$ in THF, produced (R,S)-trans-7-methoxy-2-[N-propynyl-N-ethyl(4'-fluorophenyl)amino]tetralin, 0.27 g (82% yield) as a colorless oil. $^1$H NMR (CDCl$_3$): 1.4–2.22 (5H, m), 2.70–3.00 (7H, m), 3.57 (2H, d), 3.76 (3H, s), 6.62–7.24 (7H, m).

The final product was obtained by demethylation (0.26 g, 0.77 mmol) with boron tribromide (0.92 mL) in methylene chloride at −78° C. as described above, to produce the final product, 0.18 g (75% yield) as a colorless oil. $^1$H NMR (CDCl$_3$): 1.4–2.22 (5H, m), 2.72–3.02 (7H, m), 3.58 (2H, d), 6.54–7.25 (7H, m). The free base was converted into its hydrochloride salt.

EXAMPLE 7

Synthesis of (R,S)-trans-7-Hydroxy-2-[N-propynyl-N-ethyl(thienyl)-amino]tetralin A similar reaction procedure of Example 6 was followed, but thienylacetyl chloride was employed in lieu of 4-fluorophenylacetyl chloride. Thus, (R,S)-trans-7-methoxy-2-[N-(propynyl)amino]tetralin (0.34 g, 1.5 mmol) was converted into (R,S)-trans-7-hydroxy-2-[N-propynyl-N-ethyl(thienyl)-amino]tetralin in two steps which involved reaction with thienylacetyl chloride (0.4 g, 2.3 mmol) followed by reduction of the colorless oil product (0.46 g, 57% yield) with LAH. The final compound (0.09 g, 60% yield) as a colorless oil was produced by demethylation with BBr$_3$ (0.7 mL) at −78° C. $^1$H (CDCl$_3$): 1.44–2.21 (3H, m), 2.64–3.1 (9H, m), 3.57 (2H, d), 6.55–7.11 (6H, m).

EXAMPLE 8

Synthesis of (R,S)-trans-7-Hydroxy-2-[N-propynyl-N-(3'-cyano-1'-propyl)amino]tetralin In this synthetic scheme amine, (R,S)-trans-7-methoxy-2-[N-(propynyl)amino]tetralin, 1 (0.35 g, 1.62 mmol) was reacted with 4-bromobutyronitrile (0.7 g, 4.8 mmol) in the presence of K$_2$CO$_3$ (1.2 g) in DMF. The reaction solution was warmed to 70° C. and the reaction was continued for 12 hrs. The reaction mixture was diluted with water and the product was extracted into ether layer. The crude product was chromatographed over a silica gel column and the pure product, (R,S)-trans-7-methoxy-2[N-propynyl-N-(3'-cyano-1'-propyl)amino]tetralin was eluted with (1:4) EtOAc/hexane mixture, 0.25 g (55% yield). $^1$H NMR (CDC$_3$): 1.45–3.05 (14H, m), 3.5 (2H, d), 3.79 (3H, s), 6.64–7.04 (3H, m).

The demethylation of the product (0.2 g, 0.7 mmol) was conducted in presence of boron tribromide (1 mL, 0.99 mmol) to produce final product, 0.08 g (44%) as a colorless oil (Procedure C). $^1$H NMR (CDCl$_3$): 1.22–2.06 (6H, m), 2.17–2.23 (1H, t, J=2.6 Hz), 2.35–2.49 (2H, t, J=6.9 Hz), 2.74–2.87 (5H, m), 3.46–3.48 (2H, d, J=2.4 Hz), 6.56, 6.98 (3H, m). The free base was converted into its hydrobromide salt. Anal. ($C_{17}H_{20}N_2O$. HBr)C, H, N.

Binding affinities of these novel compounds were assessed according to previously published procedures. V. J. Watts et al., EUR. J. PHARMACOL., 1993, 239,271; V. J. Watts et al., EUR. J. PHARMACOL., 1996, 50, 966. Human embryonic kidney (HEK) 293 cells were stably transfected with cDNA for the human D2L and D3 receptors by Watts and colleagues at Oregon Health Sciences University in accordance with published procedures; V. J. Watts, MOL. PHARMACOL, op. cit., and graciously shipped to the University of Illinois for receptor binding assays. Membranes were prepared from the cells as described previously, V. J. Watts et al., EUR. J. PHARMACOL., 1993, op. cit. On the average 50 (for D2L) or 135 (for D3) μg of protein was incubated with each test compound and [$^3$H]spiperone (0.4 nM) for 1 h at 30° C. in 50 mM Tris-HCl (pH 7.4), with 0.9% NaCl, and 0.025% ascorbic acid in the absence of GTP, in a total volume of 2 ml. (+)-Butaclamol (2 ,μM) was used to define nonspecific binding. Assays were terminated with a 24-pin Brandel harvester as described previously, M. E. A. Reith et al., BIOL. CHEM. 1986, 261, 7300. IC$_{50}$ values were estimated by nonlinear regression analysis with the ALLFIT equation, and converted to inhibition constants (K$_i$) by the Cheng-Prusoff equation as in previous work, Reith et al., J. BIOL. CHEM., op. cit. In this conversion, the following K$_d$ values, observed under our conditions for [$^3$H]spiperone binding, were used: 0.18 nM for D$_2$ receptors and 0.40 nM for D$_3$ receptors. The results are presented in Table 1.

TABLE 1

| Compound | R | D2L HEK Cells [$^3$H]spiperone, K$_i$ (nM) | D3 HEK Cells [$^3$H]spiperone, K$_i$ (nM) | D2L/D3L |
|---|---|---|---|---|
| (+)-7-OH-DPAT | | 533 ± 120 (5) | 5.3 ± 0.6 (6) | 101 |
| Example 4 | —(CH$_2$)$_3$—CH$_3$ | 534 ± 72 (7) | 4.9 ± 1.2 (7) | 108 |
| Example 5 | —CH$_2$—CH$_3$ | 1,492 ± 244 (5) | 13.8 ± 2.8 (5) | 108 |
| Example 6 | —(CH$_2$)$_2$—Ph—F | 1,607 ± 248 (5) | 14.5 ± 4.1 (3) | 111 |

TABLE 1-continued

| Compound | R | D2L HEK Cells [³H]spiperone, $K_i$ (nM) | D3 HEK Cells [³H]spiperone, $K_i$ (nM) | D2L/D3L |
|---|---|---|---|---|
| Example 7 | —(CH₂)₂—Th | 1,697 ± 378 (5) | 8.0 ± 0.3 (3) | 211 |
| Example 8 | —(CH₂)₃—CN | 8,307 ± 2,046 (5) | 23.5 ± 4.7 (4) | 353 |

The results in Table 1 indicate that the claimed compounds exhibit differential CNS receptor binding activity as measured by the $K_i$ in binding studies on cloned human D2L and D3 receptors in HEK cells. One skilled in the pharmaceutical arts would expect the binding activities measured in these studies to be reflected by CNS drug activity in both mammals in general, and humans in particular. The differential activity would be viewed by one skilled in the art to reflect differential activity which would be manifested behaviorally in human subjects and mammalian subjects generally.

The results show that the racemic compound of Example 4, with N-butyl and N-propynyl substitution, was about as active as the (+) isomer (the most active isomer) of 7-OH-DPAT in displacing [³H]spiperone from D3 receptors in HEK cells, despite having no-N-(n-propyl) substituent. Upon separation into its optical isomers, the compound of Example 4 would be expected to be more active than the control. In terms of differential activity, the compound of Example 4 exhibits slightly greater activity differential, even though a racemic mixture was employed.

The compound of Example 5 also exhibits high activity, though not as high as the compound of Example 4 or the control. However, its differential activity is as high as the compound of Example 4. This high activity and high differential occurs despite the absence of an n-propyl group, previously thought necessary to provide significant activity.

Compound 6 also exhibits differential activity, again about the same as the control. This compound may still be useful pharmaceutically, however, particularly as the racemic mixture and not individual stereoisomers was tested. This example underscores the differences between the subject invention N-propynyl substituted compounds and those of the prior art, which taught that one bulky N-substituent improved activity. Here, the converse is true.

The high activity and especially the high differential activity of the compounds of Examples 7 and 8 is dramatic, and different even from other compounds of the subject invention class. While having D3 receptor activity (for the racemic mixture) about the same as the control and the most active of the tested compounds, the compounds of both Examples 7 and 8 display low binding affinity for the D2L receptor as compared to the D3 receptor. The activity differentials of these compounds are more than double the activity differential of the control.

Male Sprague Dawley rats, weighing 225–275 g, were handled for 5 days prior to testing and were randomly assigned to receive one of 5 doses of Compound 6 (0–10 mg/kg, s.c.). Immediately after the injection, locomotor activity was measured for 60 min. Animals were placed into rectangular Plexiglass chambers (44×24×20 cm high) equipped with two pairs of photodetectors and light sources mounted on the front and back walls of the chamber. The light sources emitted photobeams that were 32 cm apart and 4 cm above the floor of the chamber. A computer automated system recorded the number of times the photobeams were interrupted consecutively as the animal moved from one end of the chamber to the other end.

Effects of Compound 6 on locomotor activity in comparison with the effects of 7-OH-DPAT on locomotor activity adapted from Khroyan et al. "Dose-Dependent Effects of the D3—preferring agonist 8-OH-DPAT on Motor Behaviors and Place Conditioning", PSYCHOPHARMACOL 122:351–57 (1995). Locomotor activity was measured in a novel environment for 60 and 40 min., respectively. Locomotion may expressed as the number of photobeam interruptions in drug-treated animals minus the number in vehicle-treated controls. The tested compounds exhibit some significant differences from control animals that received saline (Fisher LSD, P<0.05).

Each of the compounds within each group herein is considered to be independently disclosed. Preferred compounds are those with minimal ring substitution at $R^7$, $R^8$, $R^9$, $R^{10}$ positions. by the "ratio of differential activity" and like terms with respect to dopamine receptors, the ratio is the ratio of the respective inhibition constants $K_i$ when measured with respect to cloned D2L and D3 receptors as described herein, or by other methods which exhibit similar results with respect to binding at these sites. Binding is measured on cloned D2 and D3 receptors as described herein.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound exhibiting differential activity between dopamine receptor subtypes, said compound being an 2-aminotetralin or biosteric analog thereof containing a fused ring structure, one ring comprising an optionally ring substituted moiety or a pharmaceutically acceptable salt of said compound, wherein

X is CH₂, O, NH, or S, n is 0 or 1, and

R is ethyl, butyl, or a C₅₋₂₀ hydrocarbon, each optionally substituted by one or more halo, nitro, amino, aminoalkyl, or cyano groups, or R is a halo-, nitro-, amino-, cyano- or aminoalkyl-substituted propyl group, R optionally containing one or more heteroatoms selected from the group consisting of O, N, and S, and option- ally containing a keto, thio, ester, carbonate, urea, amide, or urethane group and where said optionally ring substituted moiety may contain one or two sites of ethylenic unsaturation.

2. A compound exhibiting differential activity between dopamine receptor subtypes of claim 1, said compound comprising a compound of the formula I or a pharmaceutically acceptable salt thereof

I wherein $R^1$ and $R^2$ together complete a 5 membered aromatic ring optionally containing up to 2 heteroatoms individually selected from the group consisting of O, N, and S, and optionally substituted by $R^3$, $R^4$, and $R^5$ at substitutable ring positions:

or a 6 membered aromatic ring optionally containing up to three heteroatoms individually selected from the group of O, N, and S, and optionally substituted by $R^3$, $R^4$, $R^5$, and $R^6$ at substitutable ring positions:

$R^3$, $R^4$, $R^5$, and $R^6$ are individually selected from H, $C_{1-18}$ alkyl, $C_{2-8}$ alkenyl, —OH, —$OR^{11}$, $NH_2$, —$NHR^{11}$, —$NHR_2^{11}$, —CN, —$SO_2H$, =O, =NH, =$NR^{11}$, —NH—CO—$NH_2$, —NH—CO—$NHR^{11}$, and NH—CO—$NR_2^{11}$, or any adjacent $R^3$ through $R^6$ may form a saturated, unsaturated, or aromatic 5 to 7 membered ring, optionally containing one to three heterocycles selected from the group consisting of N, O, and S, $R^7$, $R^8$, $R^9$, and $R^{10}$ are individually selected from H, $NR_2^{11}$, $C_{1-18}$ alkyl, $C_{2-18}$ alkenyl, $C_{3-8}$ cycloalkyl, $C_{3-8}$ cycloalkenyl, $C_{3-8}$ aryl, $C_{6-14}$ heteroalkyl $C_{1-4}$ lower alkoxy, all of said alkyl, alkenyl, cycloalkyl, cycloalkenyl, aryl, and heteroaryl groups optionally substituted by $R^{12}$ or the pair $R^7$ and $R^8$ or the pair $R^9$ and $R^{10}$ may individually as pairs be =O, —NH, or =$NHR^{11}$, where $R^{12}$ is —OH, —$OR^{11}$,

—$NHR^{11}$,

—$SO_2H$, —$SO_2R^{11}$, F, Cl, Br, $F_3C$—, —CN, or —$NO_2$, where $R^{11}$ is $C_{1-18}$ alkyl, $C_{2-18}$ alkenyl, $C_{3-8}$ cycloalkyl, $C_{3-8}$ cycloalkenyl, $C_{6-10}$ aryl, $C_{6-10}$ heteroaryl, each of R" optionally substituted by $C_{1-4}$ lower alkyl, —OH, and —$NH_2$, and wherein each alkyl, alkenyl, or cycloalkyl or alkenyl substituent may be interrupted by one or more non-adjacent heteroatoms selected from the group consisting of N, O, and S.

3. The compound of claim 2, containing a basic ring structure selected from the group consisting of:

wherein $N_R$ represents the group

4. The compound of claim 1, wherein R is selected from the group consisting of ethyl, 2-propyl, 1-butyl, 2-butyl, 3-cyanopropyl, 4'-fluorophenyl, and ethylthienyl.

5. The compound of claim 2, wherein R is selected from the group consisting of ethyl, 2-propyl, 1-butyl, 2-butyl, and 3-cyanopropyl, 4'-fluorophenyl, and ethylthienyl.

6. The compound of claim 3, wherein R is selected from the group consisting of ethyl, 2-propyl, 1-butyl, 2-butyl, 3-cyanopropyl, 4'-fluorophenyl and ethylthienyl.

7. The compound of claim 2, having the formula wherein X and Y are individually selected from the group consisting of
N, O, and S and X may also be $CH_2$, and Y may also be CH,
$R^7$, $R^8$, $R^9$, and $R^{10}$, are each individually hydrogen, $C_{1-4}$ alkyl, or $C_{1-4}$ alkoxy, or either or both of the pairs $R^7$ and $R^8$ and $R^9$ and $R^{10}$ may be replaced by =O, and wherein at least two of $R^7$ through $R^{10}$ are H, and wherein R is a $C_{2-8}$ lower alkyl, $C_{2-8}$ lower alkenyl, $C_{7-11}$ arylalkyl, $C_{6-10}$ heteroarylalkyl, said $C_{2-8}$ lower alkyl and $C_{2-8}$ lower alkenyl optionally substituted by —CN, and wherein
$R^{14}$ is $C_{1-8}$ lower alkoxy or H.

8. The compound of claim 7 wherein X is $CH_2$ and Y is CH, $R^{14}$ is H, each of $R^7$ through $R^{10}$ is H, and R is propyl, 3-cyanopropyl, 4'-fluorophenyl, or thienylethyl.

9. The compound of claim 8 which is

10. The compound of claim 8, which is

11. A process of altering central nervous system (CNS) response in a mammalian species, said process comprising administering to said mammalian species an effective response altering amount of a differential CNS activity compound being a 2-aminotetralin or biosteric analog thereof containing a fused ring structure, one ring comprising an optionally ring substituted moiety or a pharmaceutically acceptable salt or derivative of said compound, wherein
X is $CH_2$, O, NH, or S,
n is 0 or 1, and
R is a $C_{2-20}$ hydrocarbon which optionally contains one or more heteroatoms selected from the group consisting of O, N, and S, and which may contain a keto, thio, ester, carbonate, urea, amide, or urethane group.

12. The process of claim 11, said compound (I) comprising a compound of the formula or a pharmaceutically acceptable salt or derivative thereof, wherein $R^1$ and $R^2$ together complete a 5 membered aromatic ring optionally containing up to 2 heteroatoms individually selected from the group consisting of O, N, and S, and optionally substituted by $R^3$, $R^4$, and $R^5$ at substitutable ring positions:

or a 6 membered aromatic ring optionally containing up to three heteroatoms individually selected from the group of O, N, and S, and optionally substituted by $R^3$, $R^4$, $R^5$, and $R^6$ at substitutable ring positions:

$R^3$, $R^4$, $R^5$, and $R^6$ are individually selected from H, $C_{1-18}$ alkyl, $C_{2-8}$ alkenyl, —OH, —$OR^{11}$, $NH_2$, —$NHR^{11}$, —$NHR_2^{11}$, —CN, —$SO_2H$, =O, =NH, =$NR^{11}$, —NH—CO—$NH_2$, —NH—CO—$NHR^{11}$, and NH—CO—$NR_2^{11}$, or any adjacent $R^3$ through $R^6$ may form a saturated, unsaturated, or aromatic 5 to 7 membered ring, optionally containing one to three heterocycles selected from the group consisting of N, O, and S, $R^7$, $R^8$, $R^9$, and $R^{10}$ are individually selected from H, $NR_2^{11}$, $C_{1-18}$ alkyl, $C_{2-18}$ alkenyl, $C_{3-8}$ cycloalkyl, $C_{3-8}$ cycloalkenyl, $C_{3-8}$ aryl, $C_{6-14}$ heteroalkyl $C_{1-4}$ lower alkoxy, all of said alkyl, alkenyl, cycloalkyl, cycloalkenyl, aryl, and heteroaryl groups optionally substituted by $R^{12}$ or the pair $R^7$ and $R^8$ or the pair $R^9$ and $R^{10}$ may individually as pairs be =O, —NH, or =$NHR^{11}$,
where $R^{12}$ is

F, Cl, Br, $F_3C$—, —CN, or —$NO_2$,
where $R^{11}$ is $C_{1-18}$ alkyl, $C_{2-18}$ alkenyl, $C_{3-8}$ cycloalkyl, $C_{3-8}$ cycloalkenyl, $C_{6-10}$ aryl, $C_{1-10}$ heteroaryl, each of R" optionally substituted by $C_{1-4}$ lower alkyl, —OH, and —$NH_2$, and wherein each alkyl, alkenyl, or cycloalkyl or alkenyl substituent may be interrupted by one or more non-adjacent heteroatoms selected from the group consisting of N, O, and S.

13. A process of altering central nervous system (CNS) response in a mammalian species, said process comprising administering to said mammalian species an effective response altering amount of a differential CNS activity compound of claim 3.

14. The process of claim 11, wherein R is selected from the group consisting of ethyl, 1-propyl, 2-propyl, 1-butyl, 2-butyl, 3-cyanopropyl, 4'-fluorophenyl, and ethylthienyl.

15. The process of claim 12, wherein R is selected from the group consisting of ethyl, 1-propyl, 2-propyl, 1-butyl, 2-butyl, 3-cyanopropyl, 4'-fluorophenyl, and ethylthienyl.

16. The process of claim 11, wherein said compound has the formula wherein X and Y are individually selected from the group consisting of N, O, and S and X may also be $CR_2$ and Y may also be CH.

$R^7$, $R^8$, $R^9$, and $R^{10}$, are each individually hydrogen, $C_{1-4}$ alkyl, or $C_{1-4}$ alkoxy, or either or both of the pairs $R^7$ and $R^8$ and $R^9$ and $R^{10}$ may be replaced by =O, and wherein at least two of $R^7$ through $R^{10}$ are H, and wherein R is a $C_{2-8}$ lower alkyl, $C_{2-8}$ lower alkenyl, $C_{7-11}$ arylalkyl, $C_{6-10}$ heteroarylalkyl, said $C_{2-8}$ lower alkyl and $C_{2-8}$ lower alkenyl optionally substituted by —CN, and wherein
$R^{14}$ is $C_{1-8}$ lower alkoxy or H or a pharmaceutical salt or derivative thereof.

17. A process for altering the response of the dopamine D3 receptor to a greater degree than that of the dopamine D2 receptor, comprising administering to a mammalian species sufficient of a compound to provide a concentration of said compound of from 1 nM to 10 μM, said compound comprising an 2-aminotetralin or biosteric analog thereof containing a fused ring structure, one ring comprising an optionally ring substituted moiety or a pharmaceutically acceptable salt or derivative of said compound, wherein
X is $CH_2$, O, NH, or S,
n is 0, or 1, and
R is a $C_{2-20}$ hydrocarbon optionally containing one or more heteroatoms selected from the group consisting of O, N, and S, and optionally containing a keto, thio, ester, carbonate, urea, amide, or urethane group.

18. The process of claim 17, wherein the ratio of differential activity of said compound, expressed as the ratio of the inhibition constants $K_i$ for the binding affinity of D2L receptors to the inhibition constant $K_i$ for the binding affinity of D3 receptors for [$^3$H]spiperone is greater than 100.

19. The process of claim 17, wherein the ratio of differential activity of said compound, expressed as the ratio of the inhibition constants $K_i$ for the binding affinity of D2L receptors to the inhibition constant $K_i$ for the binding affinity of D3 receptors for [$^3$H]spiperone is greater than 200.

20. An aminotetralin derivative exhibiting differential binding activity with respect to D2 and D3 dopamine receptors, having the formula wherein A is hydroxyl or an ester or ether thereof in the 5- or 7- ring positions, and B is fluoro or chloro in the 6-ring position; wherein $R^{14}$ is a hydrocarbon radical selected from the group consisting of $C_{1-18}$ alkyl, $C_{2-18}$ alkenyl, $C_{2-18}$ alkenyl, $C_{3-8}$ cycloalkyl, $C_{3-8}$ cycloalkenyl, $C_{6-10}$ aryl, $C_{6-10}$ heteroaryl, $C_{7-18}$ alkaryl, $C_{7-18}$ aralkyl, $C_{7-18}$ alkheteroaryl, and $C_{7-18}$ heteroaralkyl, each of said hydrocarbon radicals optionally substituted by one or more substituents selected from the group consisting of hydroxyl, $C_{1-8}$ alkyl ester, halo, nitro, and cyano.

21. The amino tetralin derivative of claim 20, wherein $R^{14}$ is 3-cyanopropyl or ethylthienyl.

22. A method of treating a central nervous system (CNS) disorder, said method comprising administrating to a mamalian patient in need of such treating, a CNS altering amount of a compound being a 2-aminotetralin or biosteric analog thereof containing a fused ring structure, one ring comprising an optionally ring substituted moiety or a pharmaceutically acceptable salt or derivative of said compound, wherein X is $CH_2$, O, NH, or S, n is 0 or 1, and

R is $C_{2-20}$ hydrocarbon which optionally contains one or more heteroatoms selected from the group consisting of O, N, and S, and which may contain a keto, thio, ester, carbonate, urea, amide, or urethane group.

23. The method of claim 22, said compound (I) comprising a compound of the formula or a pharmaceutically acceptable salt or derivative thereof, wherein $R^1$ and $R^2$ together complete a 5 membered aromatic ring optionally containing up to 2 heteroatoms individually selected from the group consisting of O, N, and S, and optionally substituted by $R^3$, $R^4$, and $R^5$ at substitutable ring positions:

or a 6 membered aromatic ring optionally containing up to three heteroatoms individually selected from the group of O, N, and S, and optionally substituted by $R^3$, $R^4$, $R^5$, and $R^6$ at substitutable ring positions:

$R^3$, $R^4$, $R^5$, and $R^6$ are individually selected from H, $C_{1-18}$ alkyl, $C_{2-8}$ alkenyl, —OH, —$OR^{11}$, $NH_2$, —$NHR^{11}$, —$NHR_2^{11}$, —CN, —$SO_2H$, =O, =NH, =$NR^{11}$, —NH—CO—$NH_2$, —NH—CO—$NHR^{11}$, and NH—CO—$NR_2^{11}$, or any adjacent $R^3$ though $R^6$ may form a saturated, unsaturated, or aromatic 5 to 7 membered ring, optionally containing one to three heterocycles selected from the group consisting of N, O, and S, $R^7$, $R^8$, $R^9$, and $R^{10}$ are individually selected from H, $NR_2^{11}$, $C_{1-18}$ alkyl, $C_{2-18}$ alkenyl, $C_{3-8}$ cycloalkyl, $C_{3-8}$ cycloalkenyl, $C_{3-8}$ aryl, $C_{6-14}$ heteroalkyl $C_{1-4}$ lower alkoxy, all of said alkyl, alkenyl, cycloalkyl, cycloalkenyl, aryl, and heteroaryl groups optionally substituted by $R^{12}$ or the pair $R^7$ and $R^8$ or the pair $R^9$ and $R^{10}$ may individually as pairs be =O, —NH, or =$NHR^{11}$, where $R^{12}$ is

F, Cl, Br, $F_3C$—, —CN, or —$NO_2$, where $R^{11}$ is $C_{1-18}$ alkyl, $C_{2-18}$ alkenyl, $C_{3-8}$ cycloalkyl, $C_{3-8}$ cycloalkenyl, $C_{6-10}$ aryl, $C_{6-10}$ heteroaryl, each of R" optionally substituted by $C_{1-4}$ lower alkyl, —OH, and —$NH_2$, and wherein each alkyl, alkenyl, or cycloalkyl or alkenyl substituent may be interrupted by one or more non-adjacent heteroatoms selected from the group consisting of N, O, and S.

24. The method of claim 22, wherein said compound has the formula wherein X and Y are individually selected from the group consisting of N, O, and S and X may also be $CH_2$, and Y may also be CH, $R^7$, $R^8$, $R^9$, and $R^{10}$, are each individually hydrogen, $C_{1-4}$ alkyl, or $C_{1-4}$ alkoxy, or either or both of the pairs $R^7$ and $R^8$ and $R^9$ and $R^{10}$ may be replaced by =O, and wherein at least two of $R^7$ through $R^{10}$ are H, and wherein R is a $C_{2-8}$ lower alkyl, $C_{2-8}$ lower alkenyl, $C_{7-11}$ arylalkyl, $C_{6-10}$ heteroarylalkyl, said $C_{2-8}$ lower alkyl and $C_{2-8}$ lower alkenyl optionally substituted by —CN, and wherein $R^{14}$ is $C_{1-8}$ lower alkoxy or H.

25. The method of claim 24, wherein X is $CH_2$ and Y is CH, $R^{14}$ is H, each of $R^7$ through $R^{10}$ is H, and R is propyl, 3-cyanopropyl, 4'-fluorophenyl, or thienylethyl.

26. The method of claim 22, wherein said CNS disorder is a mental disorder.

27. The method of claim 22, wherein said CNS disorder is schizophrenia.

28. The method of claim 22, wherein said CNS disorder is Parkinson's disease.

29. The method of claim 22, wherein said CNS disorder is cocaine addiction.

30. The method of claim 23, wherein said CNS disorder is selected from the group consisting of mental disorder, schizophrenia, Parkinson's disease, and cocaine addiction.

31. The method of claim 25, wherein said CNS disorder is selected from the group consisting of mental disorder, schizophrenia, Parkinson's disease, and cocaine addiction.

* * * * *

UNITED STATES PATENT AND TRADEMARK OFFICE
CERTIFICATE OF CORRECTION

PATENT NO. : 7,049,337 B2
APPLICATION NO. : 10/276641
DATED : May 23, 2006
INVENTOR(S) : Dutta It is certified that error appears in the above-identified patent and that said Letters Patent is hereby corrected as shown below:

Column 17, Claim 2, line 67 to Column 18, line 15 of Patent:
(Page 7, Claim 2, line 6, of Amendment dated August 19, 2005)

Delete: " $-OH, -OR^{11}, -O-\overset{O}{\underset{\|}{C}}-R^{11}, -O-\overset{O}{\underset{\|}{C}}-R^{11}, -NHR^{11}, -O-\overset{O}{\underset{\|}{C}}-NHR^{11}, -SO_2H, -SO_2R^{11},$ "

and insert therefor: -- $-OH, -OR^{11}, -O-\overset{O}{\underset{\|}{C}}-R^{11}, -O-\overset{O}{\underset{\|}{C}}-OR'', -NHR^{11}, -O-\overset{O}{\underset{\|}{C}}-NHR^{11}, -SO_2H, -SO_2R^{11},$ --

Claim 3, column 18, lines 27 to 62 of Patent:
(Page 19, claim 32, line 1 of Amendment dated August 19, 2005)

Delete: "

Signed and Sealed this

Twenty-third Day of November, 2010

David J. Kappos
*Director of the United States Patent and Trademark Office* wherein $N_R$ represents the group and insert therefor: -- wherein $N_R$ represents the group

Column 19, claim 9, lines 35 to 49 of the Patent:
(Page 8, claim 9, line 1 of Amendment dated August 19, 2005)

Delete: "  "

and insert therefor: --  --

Column 20, claim 11, line 1 to line 9 in Patent:
(Page 9, claim 11, line 6 of Amendment dated August 19, 2005)

Delete: "  "

and insert therefor: --  --